(12) United States Patent
Miller

(10) Patent No.: US 6,758,094 B2
(45) Date of Patent: Jul. 6, 2004

(54) ULTRASONIC TRANSDUCER WAFER HAVING VARIABLE ACOUSTIC IMPEDANCE

(75) Inventor: David G. Miller, North Andover, MA (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 1 day.

(21) Appl. No.: 09/919,241

(22) Filed: Jul. 31, 2001

(65) Prior Publication Data

US 2003/0024317 A1 Feb. 6, 2003

(51) Int. Cl.[7] ............................................. H01L 41/053
(52) U.S. Cl. ........................ 73/632; 310/334; 310/336
(58) Field of Search .................... 73/628, 632, 644; 310/322, 334, 336; 367/152

(56) References Cited

U.S. PATENT DOCUMENTS

| 4,277,712 | A | * | 7/1981 | Hanafy | ........................ | 310/334 |
| 4,672,591 | A | * | 6/1987 | Breimesser et al. | ........ | 367/152 |
| 5,160,870 | A | * | 11/1992 | Carson et al. | ............... | 310/334 |
| 5,511,296 | A | * | 4/1996 | Dias et al. | ................... | 310/334 |
| 5,648,942 | A | * | 7/1997 | Kunkel, III | .................. | 367/176 |
| 5,744,898 | A | * | 4/1998 | Smith et al. | ................. | 310/334 |

* cited by examiner

Primary Examiner—John E. Chapman
(74) Attorney, Agent, or Firm—John Vodopia

(57) ABSTRACT

The invention is a wafer having variable acoustic properties. The wafer may be used as a substrate over which to form an ultrasonic transducer, an IC, or may be used as a circuit board. An ultrasonic transducer formed on the wafer may include piezoelectric ceramic transducer elements or MUT elements. By controlling the acoustic impedance of the wafer upon which the integrated control circuitry for an ultrasonic transducer is formed, the acoustic impedance of the wafer can be matched to the acoustic impedance requirements of the ultrasonic transducer. Furthermore, by the addition of internal voids, the wafer reduces or eliminates the lateral propagation of acoustic energy through the wafer.

8 Claims, 3 Drawing Sheets

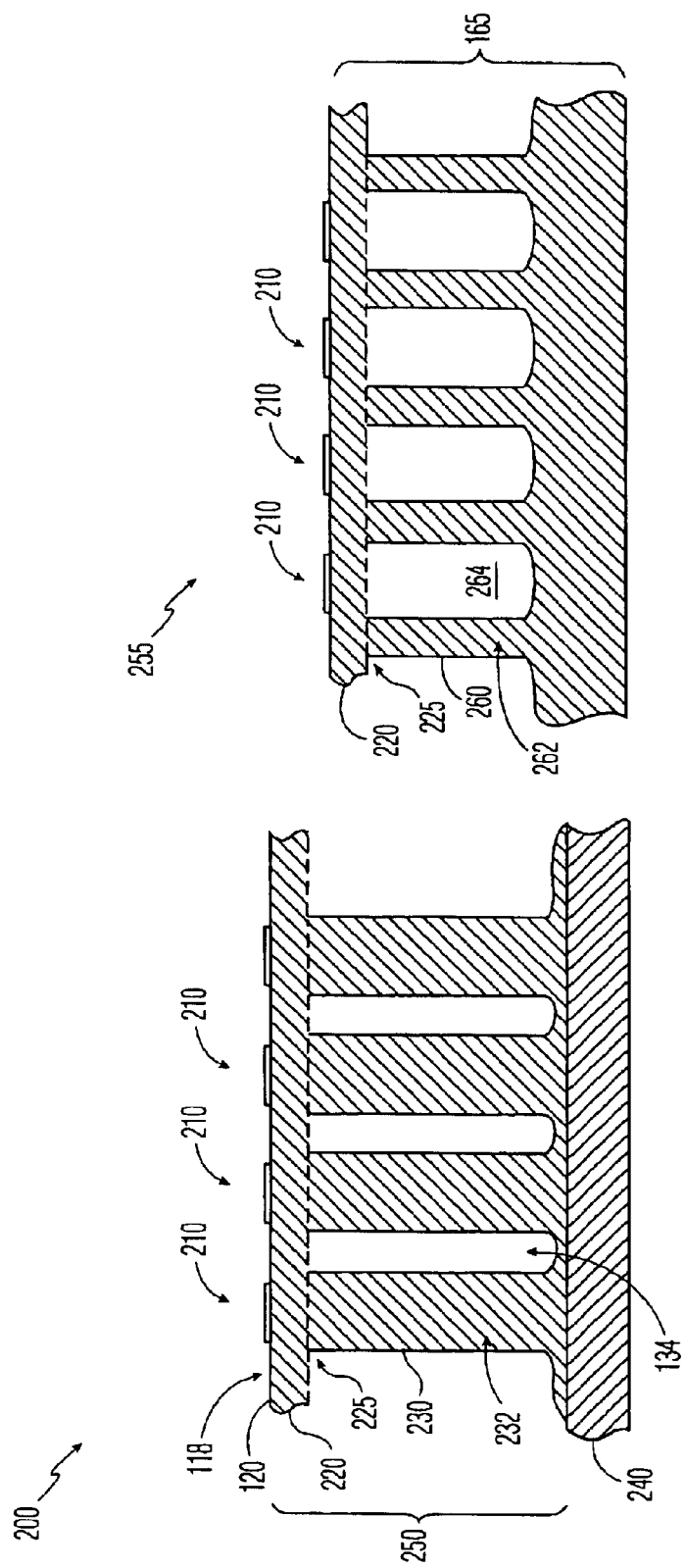

ULTRASONIC TRANSDUCER WAFER HAVING VARIABLE ACOUSTIC IMPEDANCE

TECHNICAL FIELD

The present invention relates generally to ultrasonic transducers, and, more particularly, to an ultrasonic transducer wafer, or substrate, having variable acoustic impedance.

BACKGROUND OF THE INVENTION

Ultrasonic transducers have been available for quite some time and are particularly useful for non-invasive medical diagnostic imaging. Ultrasonic transducers are typically formed of either piezoelectric elements or of micro-machined ultrasonic transducer (MUT) elements. The piezoelectric elements typically are made of a piezoelectric ceramic such as lead-zirconate-titanate (abbreviated as PZT), with a plurality of elements being arranged to form a transducer array. A MUT is formed using known semiconductor manufacturing techniques resulting in a capacitive ultrasonic transducer cell that comprises, in essence, a flexible membrane supported around its edges over a silicon substrate. By applying contact material, in the form of electrodes, to the membrane, or a portion of the membrane, and to the base of the cavity in the silicon substrate, and then by applying appropriate voltage signals to the electrodes, the MUT may be energized such that an appropriate ultrasonic wave is produced. Similarly, when electrically biased, the membrane of the MUT may be used to receive ultrasonic signals by capturing reflected ultrasonic energy and transforming that energy into movement of the electrically biased membrane, which then generates a receive signal.

The transducer elements may be combined with control circuitry forming a transducer assembly, which is then further assembled into a housing possibly including additional control electronics, in the form of electronic circuit boards, the combination of which forms an ultrasonic probe. This ultrasonic probe, having either bulk wave piezoelectric elements or MUTs and which may include various acoustic matching layers, backing layers, and de-matching layers may then be used to send and receive ultrasonic signals through body tissue.

In the past, joining an acoustic sensor, such as a piezoelectric ceramic transducer element or a MUT element, to the electrical control circuitry required the use of many individual wires to connect each element of the transducer array to the control circuitry. In the case of large transducer arrays having many hundreds or thousands of elements, large wiring harnesses were required. Unfortunately, a large wiring harness increases the bulk and the cost of the ultrasonic probe. For ultrasonic probes that are designed to be used inside the human body, it is desirable to reduce the overall size of the ultrasonic probe and related cabling. One manner of reducing the size of the probe and the cabling is to provide the transducer control electronics on an integrated circuit (IC) assembly or on a circuit board. An IC in proximity to the transducer array may be used to transmit and receive from many small transducer elements and may also be used to multiplex the signals, thereby reducing or eliminating the bulky and expensive cables that typically connect the ultrasonic probe elements to the control electronics.

Placing the transducer array over the IC results in greater packaging efficiency, but often causes undesirable coupling of acoustic energy between transducer elements through the substrate material because the substrate material on which the IC is formed comes into contact with all of the transducer elements.

Therefore, it would be desirable to have a way to connect the elements of an ultrasonic transducer array directly to an integrated circuit or circuit board while reducing or eliminating the undesirable lateral propagation of acoustic energy through the substrate of the IC and the circuit board.

SUMMARY

The invention is directed to a wafer having variable acoustic properties. The wafer may be used as a substrate over which to form an ultrasonic transducer, an IC, or may be used as a circuit board. An ultrasonic transducer formed on the wafer may include piezoelectric ceramic transducer elements or MUT elements. By controlling the acoustic impedance of the wafer upon which the integrated control circuitry for an ultrasonic transducer is formed, the acoustic impedance of the wafer can be matched to the acoustic impedance requirements of the ultrasonic transducer Furthermore, by the addition of internal voids, the wafer reduces or eliminates the lateral propagation of acoustic energy through the wafer.

Other systems, methods, features, and advantages of the invention will be or will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The present invention, as defined in the claims, can be better understood with reference to the following drawings. The components within the drawings are not necessarily to scale relative to each other, emphasis instead being placed upon clearly illustrating the principles of the present invention.

FIG. 3A is a cross-sectional schematic view illustrating a transducer constructed in accordance with an aspect of the invention and including micro-machined ultrasonic transducer (MUT) elements.

FIG. 3B is a cross-sectional schematic view illustrating an alternative embodiment of the ultrasonic transducer of FIG. 3A.

DETAILED DESCRIPTION OF THE INVENTION

The invention to be described hereafter is applicable to piezoelectric and micro-machined ultrasonic transducer (MUT) elements connected to a substrate on which an integrated circuit (IC) can be formed.

Figure 1:
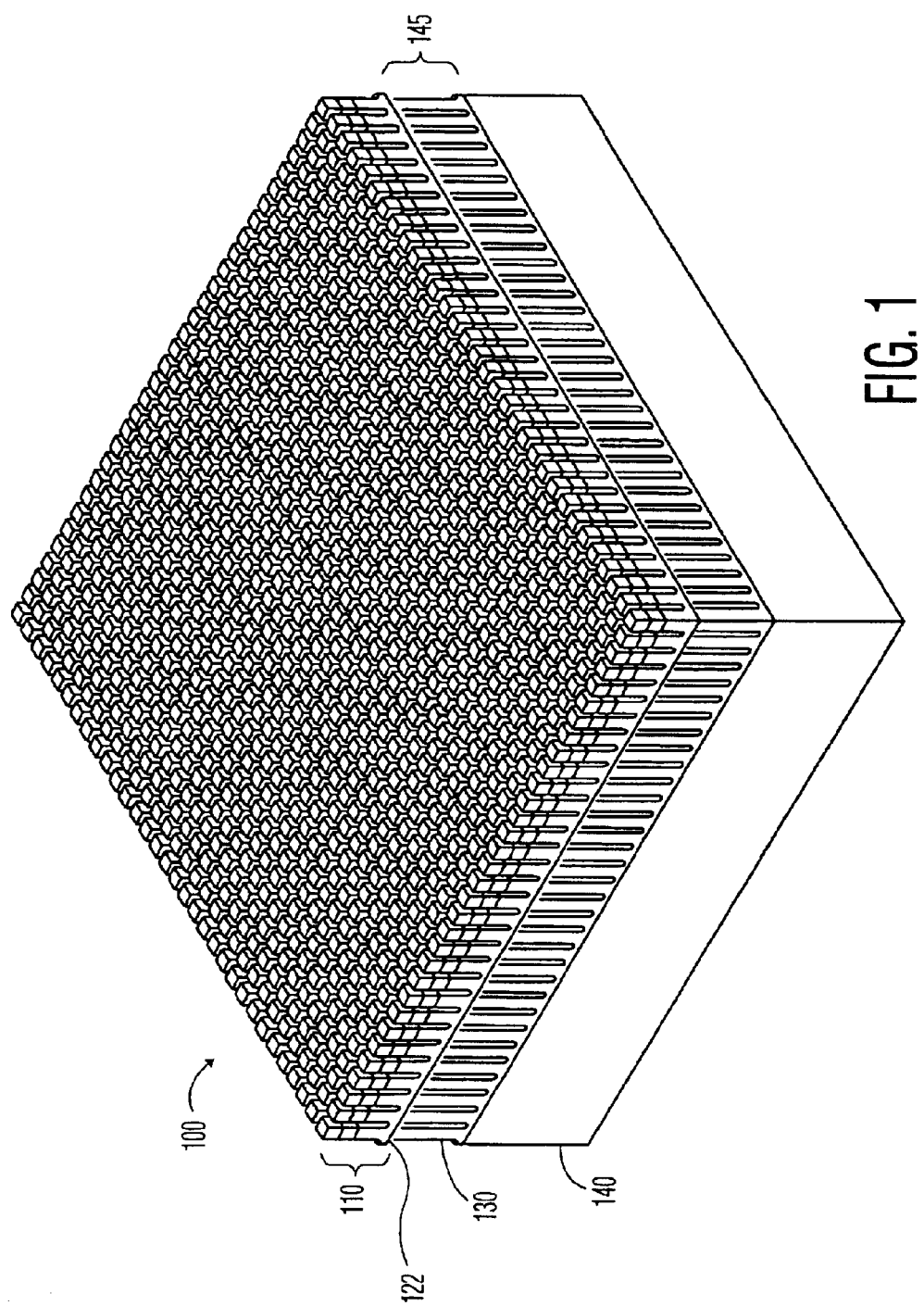
FIG. 1 is a perspective view of an ultrasonic transducer array formed on a wafer.

FIG. 1 is a perspective view of an ultrasonic transducer 100. For illustration purposes only, the ultrasonic transducer 100 comprises a plurality of elements, referred to as an array, constructed using a piezoelectric material. However, the ultrasonic transducer 100 can also be fabricated using MUT elements, as will be described below with respect to FIGS. 3A and 3B. An exemplar one of the plurality of elements is denoted by reference numeral 110. The collective plurality of transducer elements 110 comprises an ultrasonic sensor Although illustrated as uniformly spaced, the transducer elements 110 need not be spaced as illustrated. The transducer element 110 may include one or more matching layers (to be described below) and is attached to an integrated circuit (IC) (not shown in FIG. 1). In order to maximize packaging efficiency, it is desirable to assemble the transducer elements 110 over the IC. The IC can be fabricated on an acoustically variable wafer 145 constructed in accordance with an aspect of the invention. The wafer 145 can be fabricated using, for example, silicon (Si), or can alternatively be fabricated using other substrate materials such as, for example, but not limited to, germanium (Ge). As will be described below, the acoustically variable wafer 145 is formed by bonding two wafer components together. The two wafer components can also be referred to as individual wafers.

The first wafer component 130 is formed by dicing grooves with, for example, a dicing saw, or selectively etching to remove material to produce a pattern on the first wafer component 130. The pattern can be optimized for the particular application and configuration of the transducer array that will be formed over the wafer. In one embodiment the pattern includes a plurality of posts and voids. The second wafer component 122 is preferably an ultra-thin wafer and is bonded to the first wafer component 130. The first wafer component 130 and the second wafer component 122 form an acoustically variable wafer 145 having adequate stiffness and is useful for subsequent processing into any of an IC, a MUT or a circuit board with traces and vias. As will be explained in further detail below, locating the transducer array elements over the posts or the voids inside the acoustically variable wafer 145 changes the acoustic impedance experienced by each transducer element 110.

The IC is formed over the acoustically variable wafer 145. The acoustically variable wafer 145 is constructed having a variable impedance and includes an acoustically variable substrate, referred to herein as the first wafer component 130, over which is bonded a second wafer component 122. As will be described below, the first wafer component 130 includes, for example, a waffle patterned structure that allows for variable acoustic impedance. The pattern applied to the first wafer component 130 also reduces the lateral propagation of acoustic energy within the acoustically variable wafer 145. The IC can be formed on either surface of the acoustically variable wafer 145. Furthermore, instead of an IC, the acoustically variable wafer 145 could include a circuit board with traces and no active circuitry. Typically, the material from which the first wafer component 130 is formed is the same material as that of the second wafer component 122. Optionally, backing 140 can be applied behind the first wafer component 130. The backing 140 acts as an acoustic absorption material.

In accordance with an aspect of the invention, and to be described in detail below, the first wafer component 130 includes a number of cavities that define a number of support elements, referred to below as posts. The average, as well as the local, acoustic impedance of the acoustically variable wafer 145 below an array element 110 can be controlled by altering the size, quantity, shape, location, and other parameters of the cavities. Furthermore, the cavities within the first wafer component 130 reduce or eliminate the propagation of acoustic energy, or waves, traveling laterally through the acoustically variable wafer 145. This arrangement reduces the coupling of acoustic energy between the individual transducer elements 110. By varying the acoustic impedance of the acoustically variable wafer 145, the acoustic impedance of the acoustically variable wafer 145 can be matched to the acoustic impedance of the transducer elements 110. Further, by adding the cavities to the first wafer component 130, the lateral cross-coupling of acoustic energy between transducer elements 110 is significantly reduced or eliminated. Further still, by varying the acoustic impedance requirement of the acoustically variable wafer 145 to match the acoustic impedance of the transducer elements 110, the bandwidth of the ultrasonic transducer 100 can be increased.

Figure 2B:
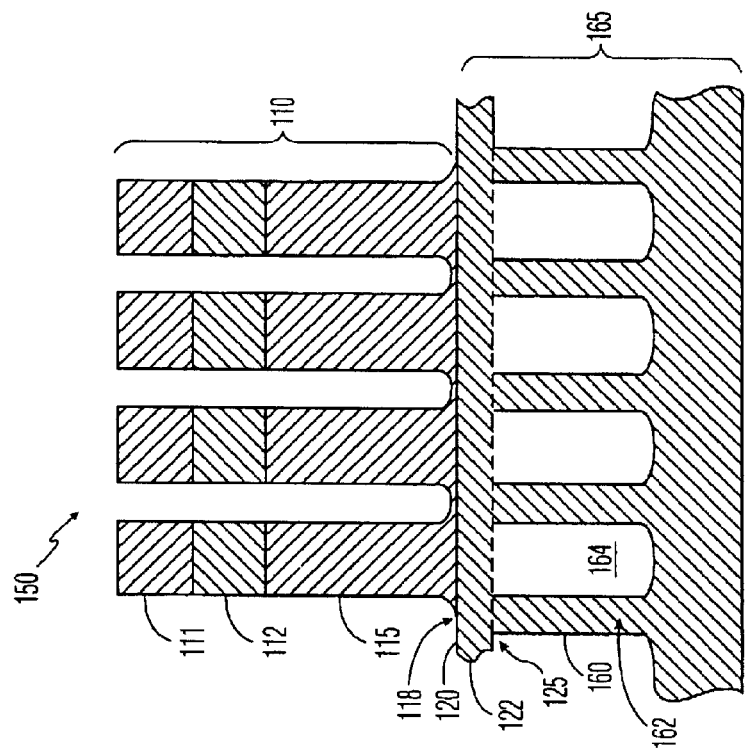
FIG. 2B is a cross-sectional schematic view illustrating an alternative embodiment of the ultrasonic transducer of FIG. 2A.
Figure 2A:
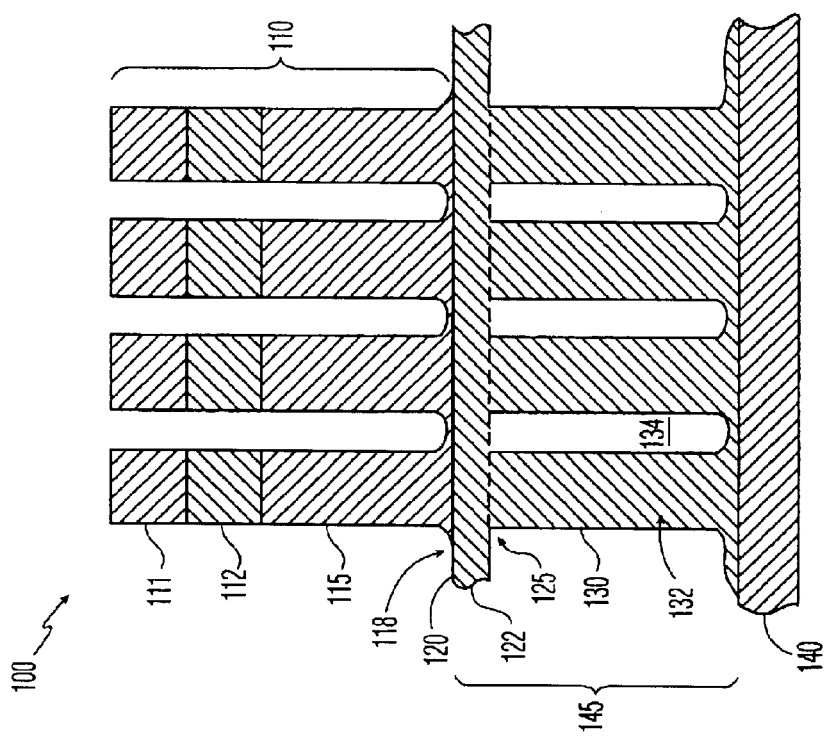
FIG. 2A is a cross-sectional schematic view of a portion of the transducer of FIG. 1.

FIG. 2A is a cross-sectional schematic view of a portion of the transducer 100 of FIG. 1. Transducer 100 includes a plurality of transducer elements 110, each of which include a first matching layer 111, a second matching layer 112, and a piezoelectric element 115. Although shown having two matching layers 111 and 112, the transducer 100 can be made with only one matching layer or with no matching layers, depending upon the desired application. The matching layer or layers, as known to those having ordinary skill in the art, help to match the acoustic impedance of the piezoelectric element 115 to the acoustic impedance of the tissue being imaged. The piezoelectric element 115 can be fabricated using all PZT ceramic, or can be fabricated using a composite piezoelectric material, depending on the desired impedance matching characteristics of the transducer.

The transducer element 110, and in particular, the piezoelectric element 115, is joined to the IC 120 along joint line 118. For purposes of explanation, the following description will assume that the IC 120 is fabricated on a surface of the acoustically variable wafer 145. The acoustically variable wafer 145 is fabricated by joining the second wafer component 122 to the first wafer component 130. The second wafer component 122 is preferably on the order of less than 200 micrometers ($\mu$m), sometimes referred to as "microns," thick and can be joined to the first wafer component 130 using, for example, anodic bonding or fusion bonding, which are well known bonding techniques.

A number of different methodologies can be used to join the piezoelectric element 115 to the IC 120, many of which are disclosed in commonly assigned U.S. Patent Application entitled "System for Attaching an Acoustic Element to an Integrated Circuit," filed on even date herewith, and assigned Ser. No. 09/919,470.

In accordance with an aspect of the invention, the first wafer component 130 includes a plurality of cavities 134, which define a plurality of pillars, or posts 132. Preferably, the cavities are cut into the first wafer component 130 using a dicing saw, or are chemically etched into the first wafer component 130 using etching techniques that are known to those having ordinary skill in the art. Preferably, the cavities 134 are formed to be approximately 50–100 micrometers ($\mu$m) wide and 250 to 450 $\mu$m deep. However, other cavity dimensions are possible, depending upon the desired acoustic properties of the acoustically variable wafer 145.

In the example shown in FIG. 2A, each transducer element 110 resides over one of the posts, 132. By altering the physical characteristics of the cavities 134 the acoustic properties of the first wafer component 130, and thus, the acoustically variable wafer 145, can be altered. In this manner, the acoustic properties of the entire ultrasonic transducer 100 can be varied, and thereby controlled. The acoustic impedance of the first wafer component 130 can be designed to match the acoustic impedance of the element 110.

In another aspect of the invention, the cavities 134 within the first wafer component 130 reduce or eliminate the propagation of acoustic waves that travel laterally through the acoustically variable wafer 145. In this manner, the coupling of acoustic energy between elements 110 through the acoustically variable wafer 145 can be significantly reduced or eliminated.

After the cavities 134 are formed in the first wafer component 130, the second wafer component 122 is joined to the first wafer component 130 along line 125, thus forming acoustically variable wafer 145. In this example, the second wafer component 122 and the first wafer component 130 are both silicon. Therefore, the second wafer component 122 can be joined to the first wafer component 130 using, for example, anodic bonding. Alternatively, fusion bonding, or other techniques known to those having ordinary skill in the art, can be used to join the second wafer component 122 to the first wafer component 130. This results in an acoustically variable wafer 145 having an acoustic impedance defined by the configuration of the cavities 134.

After the second wafer component 122 is joined to the first wafer component 130, the IC 120 is formed on the exposed surface of the second wafer component 122 using conventional IC fabrication methodologies. In profile, the IC 120 is very thin with respect to the thickness of the acoustically variable wafer 145. After the IC 120 is formed, the material that forms the piezoelectric element 115 is joined to the surface of the IC 120 along line 118 as described above. The matching layers 112 and 111 are then applied over the piezoelectric elements 115 and then the transducer elements 110 are formed by, for example, dicing or etching.

Depending on the desired characteristics of the ultrasonic transducer 100, prior to assembling the second wafer component 122 to the first wafer component 130, the cavities 134 can be filled with air or an inert gas. Alternatively, the second wafer component 122 can be joined to the first wafer component 130 in a vacuum so that the gas within the cavities 134 can be at a pressure less than that of the surrounding area.

The following discussion illustrates one manner in which the acoustic impedance of the first wafer component 130, and therefore, the acoustically variable wafer 145, can be altered to match the acoustic impedance of the transducer elements 110. Assume that silicon has an acoustic impedance of approximately 19 Mrayls (a Mrayl is unit by which acoustic impedance is measured) and piezoelectric ceramic (the material from which each piezoelectric element 115 is formed) has an acoustic impedance of approximately 33 Mrayls. Assume that it is desirable to match the acoustic impedance of the acoustically variable wafer 145 (silicon) to the acoustic impedance of the piezoelectric element 115 (piezoelectric ceramic). Reducing the impedance of the piezoelectric ceramic can be done by using a composite of piezoelectric ceramic and various polymers, having an acoustic impedance of approximately 19 Mrayls. This prevents reflections at the interface 118 between the piezoelectric element 115 and the IC 120. In accordance with an aspect of the invention, to prevent acoustic reflections at the back of the silicon interface (the surface 125 at which the second wafer component 122 is bonded to the first wafer component 130) the acoustic impedance of the acoustically variable wafer 145 can be defined, by defining the posts 132 and cavities 134, so that the acoustic impedance of the first wafer component 130 matches the acoustic impedance of the piezoelectric element 115.

Acoustic backing 140 can be added to the back of the first wafer component 130 in order to absorb any acoustic energy that migrates through the acoustically variable wafer 145.

FIG. 2B is a cross-sectional schematic view illustrating an alternative embodiment of the ultrasonic transducer 100 of FIG. 2A. Ultrasonic transducer 150, similar to that described above with respect to ultrasonic transducer 100, includes a first matching layer 111 and a second matching layer 112 over a piezoelectric element 115. The piezoelectric element 115 can be a piezoelectric ceramic, or can be a piezoelectric composite material as described above. The first matching layer 111, the second matching layer 112 and the piezoelectric element 115 comprise transducer element 110. Each transducer element 110 is attached to the IC 120 in similar manner to that described above.

In a similar manner to that described above with respect to FIG. 2A, the first wafer component 160 has a plurality of cavities 164 formed therein either by dicing, etching, or some other manner known to those having ordinary skill in the art. The cavities 164 define a plurality of posts 162. However, in the embodiment described in FIG. 2B, each transducer element 110 resides above one of the cavities 164. As mentioned above, each of the cavities 164 can be filled with air, inert gas, or can be formed having a vacuum, thus creating a vacuum or gas-backed ultrasonic transducer 150. The air-backed ultrasonic transducer 150 provides high efficiency and wide bandwidth operation. Similar to that described above, the cavities 164 can be designed to alter the acoustic impedance of the first wafer component 160, and therefore, the acoustic impedance of the acoustically variable wafer 165, and also reduce or eliminate the transmission of acoustic energy laterally through the acoustically variable wafer 165.

FIG. 3A is a cross-sectional schematic view illustrating a transducer 200 constructed in accordance with another aspect of the invention and including micro-machined ultrasonic transducer (MUT) elements. The ultrasonic transducer 200 includes an acoustically variable wafer 250 over which a plurality of MUT elements 210 are formed. Each MUT element comprises a plurality of MUT cells (not shown). The acoustically variable wafer 250 includes first wafer component 230 and a second wafer component 220, which also forms the substrate over which the MUT elements 210 are formed. The second wafer component 220 is similar to the second wafer component 122 described above, and may be silicon or another semiconductor substrate material.

In accordance with this aspect of the invention, cavities 234 are formed in the first wafer component 230, prior to joining the second wafer component 220, resulting in the acoustically variable wafer 250 having the structure shown. Each cavity 234 can be etched or cut into the first wafer component 230, creating cavities 234 that are preferably approximately 50–100 micrometers (μm) wide and 250 to 450 μm deep.

After the cavities 234 are formed in the first wafer component 230, the second wafer component 220 is bonded along line 225 to the first wafer component 230, thus forming the acoustically variable wafer 250. After the acoustically variable wafer 250 is thus formed, the MUT elements 210 are fabricated over a surface of the acoustically variable wafer 250 as known to those having ordinary skill in the art. The first wafer component 230 can be either silicon or any other substrate depending upon the acoustic performance desired of the ultrasonic transducer 200. The second wafer component 220 can be bonded to the first wafer component 230 using, for example, anodic bonding or fusion bonding. Furthermore, in this example, other silicon to silicon bonding techniques can be used.

As described above, the cavities 234 can be filled with air, gas or can contain a vacuum in order to provide acoustic isolation and greatly reduce or eliminate any acoustic energy traveling laterally in the acoustically variable wafer 250. This greatly reduces acoustic coupling, thus reducing acoustic cross-talk between MUT elements 210. As shown in FIG. 3A, each MUT element 210 resides over one of the post 234. By altering the size, shape, location and quantity of the cavities 234, the acoustic impedance of the first wafer component 230, and in particular, the acoustic impedance of each post 232, can be designed to match the acoustic impedance of a MUT transducer element to a range of backing materials. As described above, backing 240 can be applied to the first wafer component 230 to absorb any acoustic energy that travels through the acoustically variable wafer 250.

FIG. 3B is a cross-sectional schematic view illustrating an alternative embodiment 255 of the ultrasonic transducer 200 of FIG. 3A. As shown in FIG. 3B, the first wafer component 260 includes a plurality of cavities 264, which define a plurality of posts 262. However, in this embodiment, each MUT element 210 resides over one of the cavities 264.

It will be apparent to those skilled in the art that many modifications and variations may be made to the present invention, as set forth above, without departing substantially from the principles of the present invention. For example, the present invention can be used with piezoelectric ceramic and MUT transducer elements. Furthermore, the invention is applicable to different substrate materials including, for example, silicon and germanium. All such modifications and variations are intended to be included herein.

What is claimed is:

1. An ultrasonic transducer, comprising:

an ultrasonic sensor having a plurality of transducer elements formed on a first wafer component; and an integrated circuit formed on a second wafer component, said second wafer component including a plurality of cavities defining a plurality of posts such that the cavities are configured and dimensioned to alter the acoustic impedance of said second wafer component in a predefined manner, and wherein the integrated circuit is joined to the ultrasonic sensor on said first wafer component and wherein each of the elements of the ultrasonic sensor is located over a respective one of the plurality of cavities.

2. The transducer of claim 1, wherein the ultrasonic sensor comprises piezoelectric ceramic material.

3. The transducer of claim 1, wherein the ultrasonic sensor comprises a micro-machined ultrasonic transducer (MUT).

4. The transducer of claim 1, wherein the cavities reduce acoustic energy traveling laterally in the wafer.

5. The transducer of claim 1, wherein the wafer is silicon.

6. The transducer of claim 1, wherein the wafer is germanium.

7. The transducer of claim 1, wherein the cavities are designed to allow the acoustic impedance of the wafer to match the acoustic impedance of the transducer elements.

8. The transducer of claim 1, wherein the cavities are configured and dimensioned in a predetermined manner for the purpose of altering the acoustic impedance of the wafer to increase the effective bandwidth of the transducer elements.

* * * * *